United States Patent [19]

Hanes

[11] Patent Number: 4,721,820
[45] Date of Patent: Jan. 26, 1988

[54] PROCESS FOR THE ISOMERIZATION OF ALLYLIC ETHERS

[75] Inventor: Ronnie M. Hanes, Milford, Ohio

[73] Assignee: National Distillers and Chemical Corporation, New York, N.Y.

[21] Appl. No.: 944,081

[22] Filed: Dec. 22, 1986

[51] Int. Cl.$^4$ .............................................. C07C 41/32
[52] U.S. Cl. .................... 568/689; 568/384; 568/627; 568/687; 568/688; 568/690
[58] Field of Search ............... 568/627, 384, 687, 688, 568/689, 690

[56] References Cited

U.S. PATENT DOCUMENTS 3,755,451  8/1973  Kurtz et al. .......................... 568/687

Primary Examiner—Howard T. Mars
Attorney, Agent, or Firm—Kenneth D. Tremain

[57] ABSTRACT

A process for isomerizing allylic ethers is disclosed. In this process a compound having the structural formula $$CH_2=CH-CH(OR)-R^1$$

where R is hydrocarbyl; and $R^1$ is an organo group is contacted with a hydroxy-containing compound and a catalytically effective amount of a catalyst selected from the group consisting of cupric chloride, cupric bromide, a mixture of cupric chloride and palladium chloride, a mixture of cupric chloride and palladium bromide, a mixture of cupric bromide and palladium chloride and a mixture of cupric bromide and palladium bromide whereby a compound having the structural formula $$RO-CH_2-CH=CH-R^1$$

where R and $R^1$ have the meanings given above is formed.

21 Claims, No Drawings

PROCESS FOR THE ISOMERIZATION OF ALLYLIC ETHERS

BACKGROUND OF THE DISCLOSURE

1. Field of the Invention

The instant invention is directed to a process for isomerizing an allylic ether. More specifically, the present invention is directed to a process wherein an allylic ether is isomerized such that the allylic ether functional group, remote from the terminal end of the compound, is isomerized so that it becomes the terminal functional group.

2. Background of the Prior Art

Allylic ethers are well known reactive compounds wherein the functional allylic ether group reacts with a whole host of reactive groups. Those skilled in the art are aware of the greater utility of allylic ether compounds containing an allylic ether group on the terminal carbon atom compared to those compounds where the allylic ether group is on a non-terminal carbon atom. This increased utility of allylic ether compounds possessing terminal reactive allylic ether groups is due to the use of such compounds as intermediates in the synthesis of commercial products.

Although allylic ether compounds having terminal functional allylic ether groups are known in the art to possess far more commercial importance than allylic ether compounds whose allylic ether groups are substituted on a non-terminal carbon atom, oftentimes synthesis routes which result in the formation of an allylic ether compound effect such less useful compounds in which the functional allylic ether group is positioned on a non-terminal carbon atom.

An important example of the above remarks is provided by the synthesis of azelaic acid, a commercially important product. Azelaic acid can be synthesized from an allylic ether-containing octadiene in which the allylic ether group is bonded to the terminal carbon atom of the octadiene chain. The usual synthesis of an alkoxy-containing octadiene allylic ether starts with butadiene. The reaction of butadiene produces an alkoxy-containing octadiene wherein the alkoxy group, that is, the allylic ether group, is positioned on a non-terminal carbon atom. Thus, an isomerization process to transfer the allylic ether group from a non-terminal carbon atom of the octadiene chain to a terminal carbon atom on that chain would, in itself, establish an important advance in the art.

Allylic ether group rearrangement of allylic ether compounds are very uncommon in the art. Although isomerization of allylic ester compounds is known, there is little in the art directed to the rearrangement of allylic ethers compounds. Takahashi et al., Bull. Chem. Soc. Japan 45, 230 (1972) presents the closest known art relating to a process for rearranging allylic ethers wherein an allylic ether group is moved to the terminal carbon from another position on the compound chain. In Takahashi et al. a catalyst comprising a mixture of dichlorobis-(triphenylphosphine)palladium (II) and sodium phenoxide is used to catalytically isomerize octadienes having allylic ether functionality. As suggested by the catalyst used, the teaching of Takahashi et al. is limited to the utilization of a Group VIII metal catalyst, specifically, palladium. It is, furthermore, noted that in the case where the allylic ether group is aliphatic, the yields obtained are very low.

U.S. Pat. No. 2,429,411 discloses a process for synthesizing an unsaturated ether which may be allylic. However, the starting reactant is not an allylic ether but rather a dienol. The process involves the use of a mineral acid catalyst. Such a process is far removed from the isomerization of an allylic ether to produce an isomer allylic ether compound possessed of terminal functionality in the presence of a metal-containing catalyst.

U.S. Pat. No. 3,755,450 to Kurtz et al. teaches a method for isomerizing octyl compounds by catalytic conversion of the octyl compound in the presence of a palladium catalyst complex with triphenylphosphine. The '451 patent is directed to allylic alkenyl ethers, including allyl octadienyl ether. It is emphasized that this specific reaction is one of literally hundreds of possibilities within the scope of the teaching of this patent. It is furthermore emphasized that no teaching, disclosure or suggestion is made of utilizing a metal-containing catalyst system which includes copper.

The above remarks establish the need in the art for a new process for isomerizing allylic ethers such that the allylic ether group is moved from a non-terminal to a terminal carbon atom. The above discussion, furthermore, establishes not only the need in the art of a commercial process for conducting such a transformation but, moreover, the requirement for a process in which such a process is conducted without the necessity of using very expensive palladium-containing catalysts.

SUMMARY OF THE INVENTION

A new process has now been discovered for isomerizing a compound having allylic ether functionality on a non-terminal carbon atom to produce an allylic ether compound possessed of allylic ether functionality on a terminal carbon atom. This process not only produces that important result but does so in a commercially feasible process providing relatively high yield. The new process of the present invention is furthermore characterized by the use of a low cost catalyst system.

In accordance with the present invention a new process for isomerizing allylic ethers is provided. In this process a compound having the structural formula $$CH_2=CH-CH(OR)-R^1$$

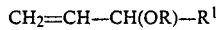

where R is hydrocarbyl and $R^1$ is an organo group is contacted with a hydroxy-containing compound and a catalytically effective amount of a catalyst selected from the group consisting of cupric chloride, cupric bromide, a mixture of cupric chloride and palladium chloride, a mixture of cupric chloride and palladium bromide, a mixture of cupric bromide and palladium chloride and a mixture of cupric bromide and palladium bromide whereby a product having the structural formula $$RO-CH_2-CH=CH-R^1$$

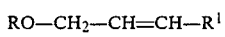

where R and $R^1$ have the meanings given above.

DETAILED DESCRIPTION

The present invention is directed to a process for isomerizing allylic ethers. In this process an allylic ether having the structural formula $$CH_2=CH-CH(OR)-R^1 \qquad (I)$$

where R is hydrocarbyl; and $R^1$ is an organo group is isomerized.

More preferably, the allylic ether isomerized in the process of the present invention is characterized by structural formula I where R is alkyl, aryl, alkenyl, aralkyl, alkaryl or alkynyl; and R¹ is alkyl, aryl, alkenyl, aralkyl, alkaryl, acyl, aralkenyl or alkenylaryl.

Still more preferably, the allylic ether reacted in the present invention is defined by structural formula I where R is alkyl, aryl or aralkyl; and R¹ is alkyl, alkenyl, or aralkenyl.

Even more preferably, the starting allylic ether of the present invention has the structural formula I where R is alkyl or aryl; and R¹ is alkenyl or aralkenyl.

Yet, still more preferably, the allylic ether of the present invention to be rearranged is characterized by structural formula I where R is alkyl, especially $C_1$-$C_5$ alkyl; and R¹ is alkenyl, especially $C_1$-$C_8$ alkenyl.

Most preferably, the allylic ether reactant of the present invention is defined by structural formula I where R is $C_1$-$C_2$ alkyl; and $R_1$ is $C_6$-$C_7$ alkenyl.

The allylic ether of the present invention is contacted with a hydroxy-containing compound. The hydroxy-containing compound of the instant invention is any organic compound possessed of at least one hydroxy group. Thus, the hydroxy-containing compound of the present invention may be an alkanol, cycloalkanol, an aliphatic polyol, an arylol or an arylpolyol.

More preferably, the hydroxy-containing compound of the present invention is an alkanol, a cycloalkanol, a naphthol, a phenol or an alkylene glycol.

Still more preferably, the hydroxy-containing compound of the present invention is an alkanol or an alkylene glycol.

Even more preferably the hydroxy-containing compound is an alkanol, especially $C_1$-$C_4$ alkanol. Of the $C_1$-$C_4$ alkanols within the contemplation of the present invention methanol, ethanol and isopropanol are particularly preferred.

Most preferably, the hydroxy-containing compound of this invention of the process of this invention is methanol.

In addition to the hydroxy-containing compound, the allylic ether, characterized by structural formula I, is contacted with a catalytically effective amount of a catalyst selected from the group consisting of cupric chloride, cupric bromide, a mixture of cupric chloride and palladium chloride, a mixture of cupric chloride and palladium bromide, a mixture of cupric bromide and palladium chloride and a mixture of cupric bromide and palladium bromide.

More preferably, the catalyst utilized in the process of the present invention is selected from the group consisting of cupric chloride and a mixture of cupric chloride and palladium chloride.

In the preferred embodiment wherein the catalyst is a mixture of cupric chloride and palladium chloride, it is preferred that the weight ratio of cupric chloride to palladium chloride be in the range of between about 1:1 and 1,000:1; more preferably, between about 5:1 and 100:1; still more preferably, between 10:and 50:1 and most preferably between 15:1 and 25:1.

The product of the present invention is an allylic ether having the structural formula

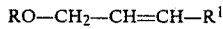    (II)

where R and R¹ have the definitions given above. The product obtained in each of the more preferred embodiments is defined by the meanings of R and R¹ given in each of these embodiments of structural formula I.

Of the multiplicity of allylic ethers defined by structural formula I, within the contemplation of this invention, a particularly preferred class of such ethers are the alkoxy-substituted octadienes which may or may not be substituted with an additional alkyl group. Of particular appliation is the isomerization of the allyllic ether, 3-methoxy-1,7-octadiene to procuce an isomer allylic ether thereof, 8-methoxy-1,6-octadiene. The later allylic ether, of course, is an allylic ether with the ether group on the terminal carbon atom, in accordance with structural formula II. In this preferred embodiment of the present invention, the hydroxy-containing compound, which contacts the octadiene reactant in the presence of a catalyst, is an alkanol, preferably methanol. The catalyst, in this reaction, is preferably cupric chloride of a mixture of cupric chloride and palladium chloride. Of these, a mixture of cupric chloride and palladium chloride is particularly preferred.

The process of the present invention is preferably conducted at a temperature in the range of between about 75° C. and 175° C. More preferably, the temperature of reaction is in the range of between about 100° C. and 150° C. Most preferably, the isomeric reaction occurs at a temperature in the range of between about 115° C. and about 135° C.

The pressure of the process of the present invention is that pressure consistent with the temperature of reaction. That is, the pressure is that pressure consistent with the desired temperature and the maintenance of the hydroxy-containing compound in the liquid state. Usually, the pressure is preferably autogenous pressure. Thus, it is preferred that the pressure of the process of this invention be in the range of between about 35 pounds per square inch gauge (psig) and about 200 psig. More preferably, the pressure of the process of the present invention is in the range of between about 50 psig and about 150 psig. Most preferably, the process of the subject invention is conducted at a pressure in the range of between about 75 psig and about 125 psig.

To better appreciate the process of the present invention, the following examples are given. These examples are given for illustrative purposes only. Therefore, the invention should not be deemed limited thereto.

EXAMPLE 1

A 500 cc. stirred, polytetrafluoroethylene-lined Berghof [trademark] reactor was charged with 0.15 g. palladium chloride; 1.25 g. cupric chloride; 70 ml. 3-methoxy 1,7-octadiene; 70 ml. methanol; and 20 ml. methyl benzoate (a gas chromotography standard). The reactor and its contents were heated to 125° C. and pressurized to about 3.5 bars. The reactor was maintained at these thermodynamic conditions for 2 hours. The reaction mass was analyzed, by gas chromotographic means, at 30 minute intervals during the duration of the run. The results of this example appear below in Table 1.

In addition to the results tabulated in Table 1 it was noticed that the reaction turned progressively darker during the run. Thus, the initial clear yellow color of the reaction mass before the start of the run turned progressively darker until it was dark brown by the end of the two-hour period of reaction.

TABLE 1
EXPERIMENTAL OBSERVATIONS

| | Millimoles in Reaction Mass At | | | | |
|---|---|---|---|---|---|
| | 0 time | 30 min. | 60 min. | 90 min. | 120 min. |
| Allylic Ether | | | | | |
| 3-MEOD* | 407.3 | 272.4 | 184.3 | 134.5 | 117.5 |
| 8-MEOD** | 12.2 | 121.6 | 154.1 | 183.5 | 194.8 |
| CALCULATED RESULTS | | | | | |
| % Conversion of 3-MEOD | | 33.1 | 54.8 | 67.0 | 71.2 |
| % Selectivity to 8-MEOD | | 90 | 69 | 67 | 67 |

Footnotes
*3-MEOD is 3-methoxy-1,7-octadiene
**8-MEOD is 8-methoxy-1,6-octadiene

EXAMPLE 2

Example 1 was repeated but for the temperature and pressure of the run. In this example the temperature of the Berghof [trademark] reactor was raised to 150° C. and the pressure elevated to about 9.0 bars. Again, the reaction mass started out as clear yellow and progressively darkened to a dark brown color.

The quantitative results of this example are summarized below in Table 2. In that the reaction, at these conditions, was more rapid than Example 1 an additional sample was taken at 15 minutes into the run.

TABLE 2

| | Millimoles in Reaction Mass At | | | | | |
|---|---|---|---|---|---|---|
| | 0 time | 15 min. | 30 min. | 60 min. | 90 min. | 120 min. |
| EXPERIMENTAL RESULTS | | | | | | |
| Allylic Ether | | | | | | |
| 3-MEOD | 329.7 | 258.7 | 190.1 | 129.2 | 112.5 | 99.77 |
| 8-MEOD | 28.30 | 83.43 | 124.79 | 142.63 | 138.71 | 127.13 |
| CALCULATED RESULTS | | | | | | |
| % Conversion of 3-MEOD | | 21.5 | 42.4 | 60.8 | 65.9 | 69.8 |
| % Selectivity to 8-MEOD | | 78 | 69 | 57 | 51 | 43 |

EXAMPLE 3

Example 1 was repeated except that in this run the Berghof [trademark] reactor was purged four times with nitrogen gas. Moreover, whereas the pressure in Example 1 represented the vapor pressure of the reaction mass, in this run, although the temperature of the reaction was again 125° C., nitrogen gas was used to provide the pressure under which the reaction occurred, 100 pounds per square inch gauge (psig).

As in Example 1 the clear yellow color of the reaction mass at the start of the reaction turned progressively darker brown as the reaction continued. A summary of the example is provided in tabular form in Table 3.

TABLE 3

| | Millimoles in Reaction Mass At | | | | | |
|---|---|---|---|---|---|---|
| | 0 time | 15 min. | 30 min. | 60 min. | 90 min. | 120 min. |
| EXPERIMENTAL RESULTS | | | | | | |
| Allylic Ether | | | | | | |
| 3-MEOD | 374.3 | 332.8 | 210.0 | 154.7 | 138.9 | 132.1 |
| 8-MEOD | 0.35 | 63.91 | 139.18 | 165.73 | 174.14 | 169.61 |
| CALCULATED RESULTS | | | | | | |
| % Conversion of 3-MEOD | | 11.1 | 43.9 | 58.7 | 62.9 | 64.7 |
| % Selectivity to 8-MEOD | | 71 | 85 | 75 | 74 | 70 |

EXAMPLE 4

Example 3 was repeated but for a doubling in the concentration of palladium chloride. That is, 0.30 g. of PdCl₂ was employed in the run. The time of the run was extended to 4 hours with sampling every 15 minutes during the first hour.

As in Example 3 the reaction samples turned progressively darker brown with time. The results of the run are summarized in Table 4.

TABLE 4

| | Millimoles in Reaction Mass At | | | | | | | |
|---|---|---|---|---|---|---|---|---|
| | 0 time | 15 min. | 30 min. | 45 min. | 60 min. | 90 min. | 120 min. | 240 min. |
| EXPERIMENTAL RESULTS | | | | | | | | |
| Allylic Ether | | | | | | | | |
| 3-MEOD | 358.8 | 259.1 | 173.2 | 143.8 | 123.1 | 111.0 | 101.11 | 114.2 |
| 8-MEOD | 0.51 | 103.72 | 144.06 | 158.01 | 172.51 | 165.59 | 159.73 | 151.06 |
| CALCULATED RESULTS | | | | | | | | |
| % Conversion of 3-MEOD | | 27.8 | 51.7 | 59.9 | 65.7 | 69.1 | 71.8 | 68.2 |
| % Selectivity to 8-MEOD | | 100 | 78 | 73 | 73 | 67 | 62 | 62 |

EXAMPLE 5

Example 3 was repeated but for a reduction in temperature to 100° C. The example was run for 4 hours with sampling every 15 minutes during the first hour and every 30 minutes thereafter.

The samples, which at 0 time were clear yellow, turned dark brown 30 minutes into the run. A tabular summary of the run is provided in Table 5.

TABLE 5

| | \multicolumn{11}{c}{Millimoles in Reaction Mass At} |
|---|---|---|---|---|---|---|---|---|---|---|---|
| | 0 | 15 | 30 | 45 | 60 | 90 | 120 | 150 | 180 | 210 | 240 min. |
| | | | | EXPERIMENTAL RESULTS | | | | | | | |
| Allylic Ether | | | | | | | | | | | |
| 3-MEOD | 377.7 | 323.8 | 193.8 | 172.4 | 164.8 | 154.6 | 140.6 | 130.6 | 124.6 | 123.6 | 118.8 |
| 8-MEOD | 6.95 | 53.31 | 145.10 | 150.22 | 155.90 | 171.49 | 178.52 | 187.05 | 183.39 | 178.75 | 188.59 |
| | | | | CALCULATED RESULTS | | | | | | | |
| % Conversion of 3-MEOD | | 14.3 | 48.7 | 54.4 | 56.4 | 59.1 | 62.8 | 65.4 | 67.0 | 67.3 | 68.5 |
| % Selectivity to 8-MEOD | | 86 | 79 | 73 | 73 | 77 | 75 | 82 | 70 | 68 | 70 |

EXAMPLE 6

Example 3 was repeated except that no palladium chloride was charged into the reactor. The catalyst thus consisted of 1.25 g. of cupric chloride. Otherwise, the run was identical with Example 3 but for continuation of this example for 3 hours with sampling (gas chromatography analysis) every 15 minutes during the first hour and at 30 minute intervals thereafter.

A summary of this run is provided in Table 6.

TABLE 6

| | \multicolumn{8}{c}{Millimoles in Reaction Mass At} |
|---|---|---|---|---|---|---|---|---|
| | 0 | 15 | 30 | 45 | 60 | 90 | 120 | 150 | 180 min. |
| | | | | EXPERIMENTAL RESULTS | | | | | |
| Allylic Ether | | | | | | | | | |
| 3-MEOD | 382.2 | 393.5* | 264.1 | 198.1 | 184.5 | 178.2 | 166.8 | 169.1 | 164.4 |
| 8-MEOD | 0.81 | 25.37 | 115.47 | 148.10 | 167.04 | 161.83 | 172.58 | 179.61 | 174.09 |
| | | | | CALCULATED RESULTS | | | | | |
| % Conv. of 3-MEOD | | 6 | 30.9 | 48.2 | 51.7 | 53.4 | 56.4 | 55.8 | 57.0 |
| % Select. to 8-MEOD | | 100 | 98 | 75 | 84 | 79 | 80 | 84 | 80 |

EXAMPLE 7

Example 6 was repeated except for a variation in thermodynamic conditions. Like Example 6, this run was conducted under nitrogen pressure. However, the pressure of this run was increased to 135 psig (Example 6 was run at 100 psig). In addition, the temperature was raised to 150° C.

This cupric chloride catalyzed run is tabulated in Table 7.

EXAMPLE 8

Example 3 was repeated except for the concentration of the catalyst. The concentration of the cupric chloride component of the catalyst was doubled to 2.50 g. The concentration of palladium chloride remained the same (0.15 g).

The result of this run are included in Table 8.

TABLE 8

| | \multicolumn{7}{c}{Millimoles in Reaction Mass At} |
|---|---|---|---|---|---|---|---|
| | 0 time | 15 min. | 30 min. | 45 min. | 60 min. | 90 min. | 120 min. |
| | | | EXPERIMENTAL RESULTS | | | | |
| Allylic Ether | | | | | | | |
| 3-MEOD | 325.4 | 188.1 | 102.8 | 88.0 | 89.3 | 89.41 | 82.03 |
| 8-MEOD | 46.07 | 85.51 | 123.76 | 130.74 | 125.70 | 124.49 | 127.60 |
| | | | CALCULATED RESULTS | | | | |
| % Conversion of 3-MEOD | | 42.2 | 68.4 | 73.0 | 72.6 | 72.5 | 74.8 |
| % Selectivity to 8-MEOD | | 62 | 56 | 55 | 34 | 33 | 33 |

EXAMPLE 9

A 71 cc. glass-lined Parr [trademark] bomb was charged with 0.0052 g. palladium chloride; 0.0514 g. cupric chloride; 3 ml. methanol; and 3 ml. 3-methoxy-1,7-octadiene. The charged bomb was purged three times with carbon monoxide gas and pressurized to 200 psig with carbon monoxide. The bomb was then deposited in a shaker oven maintained at 100° C. for six hours.

A gas chromatography analysis of the product revealed that 57% of the 3-methoxy-1,7-octadiene was converted to 8-methoxy-1,6-octadiene.

TABLE 7

| | \multicolumn{8}{c}{Millimoles in Reaction Mass At} |
|---|---|---|---|---|---|---|---|---|
| | 0 | 15 | 30 | 45 | 60 | 90 | 120 | 150 | 180 minutes |
| | | | | EXPERIMENTAL RESULTS | | | | | |
| Allylic Ether | | | | | | | | | |
| 3-MEOD | 384.8 | 258.9 | 216.1 | 204.8 | 197.9 | 189.7 | 187.1 | 185.7 | 182.4 |
| 8-MEOD | 20.64 | 91.27 | 120.67 | 126.27 | 131.96 | 125.21 | 126.67 | 127.62 | 134.99 |
| | | | | CALCULATED RESULTS | | | | | |
| % Conversion of 3-MEOD | | 32.7 | 43.8 | 46.8 | 48.6 | 50.7 | 51.4 | 51.7 | 52.6 |
| % Selectivity to 8-MEOD | | 72 | 71 | 70 | 71 | 71 | 64 | 54 | 57 |

COMPARATIVE EXAMPLE 1

Example 9 was repeated except that the amount of palladium chloride was minutely changed to 0.0046 g. and, in a major change, no cupric chloride was included in the charged bomb.

A gas chromotographic analysis of the reaction product, after 6 hours exposure to a shaker oven set at 100° C. and a pressure of 200 psig, indicated that none of the 3-methoxy-1,7-octadiene was converted to 8-methoxy-1,6-octadiene.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for isomerizing an allylic ether comprising contacting a compound having the structural formula $$CH_2=CH-CH(OR)-R^1$$

where R is hydrocarbyl and $R^1$ is an organo group with a hydroxy-containing compound and a catalytically effective amount of a catalyst selected from the group consisting of cupric chloride, cupric bromide, a mixture of cupric chloride and palladium chloride, a mixture of cupric chloride and palladium bromide, a mixture of cupric bromide and palladium chloride and a mixture of cupric bromide and palladium bromide whereby a product, having the structural formula $$RO-CH_2-CH=CH-R^1$$

where R and $R^1$ have the meanings given above, is formed.

2. A process in accordance with claim 1 wherein R alkyl, aryl, alkenyl, aralkyl, alkaryl or alkynyl; and $R^1$ is alkyl, aryl, alkenyl, aralkyl, alkaryl, acyl, aralkenyl or alkenylaryl and said hydroxy-containing compound is an alkanol, a cycloalkanol, an aliphatic polyol, an arylol or an arylpolylol.

3. A process in accordance with claim 2 wherein R is alkyl, aryl or aralkyl; $R^1$ is alkyl, alkenyl or aralkenyl and said hydroxy containing compound is an alkanol, a cycloalkanol, a phenol or an alkylene glycol.

4. A process in accordance with claim 3 wherein R is alkyl or aryl; and $R^1$ is alkenyl or aralkenyl and said hydroxy-containing compound is an alkanol or an alkylene glycol.

5. A process in accordance with claim 4 wherein R is alkyl; and $R^1$ is alkenyl and said hydroxy-containing compound is an alkanol.

6. A process in accordance with claim 5 wherein R is $C_1-C_5$ alkyl; and $R^1$ is $C_1-C_8$ alkenyl and said hydroxy-containing compound is $C_1-C_4$ alkanol.

7. A process in accordance with claim 6 wherein R is $C_1-C_2$ alkyl; and $R^1$ is $C_6-C_7$ alkenyl and said $C_1-C_4$ alkanol is methanol, ethanol or isopropanol.

8. A process in accordance with claim 1 wherein said catalyst is cupric chloride.

9. A process in accordance with claim 1 wherein said catalyst is a mixture of cupric chloride and palladium chloride.

10. A process in accordance with claim 9 wherein the weight ratio of said cupric chloride to said palladium chloride is in the range of between about 1:1 and about 1000:1.

11. A process in accordance with claim 1 wherein said isomerization reaction occurs at a temperature in the range of between about 75° C. and about 175° C.

12. A process in accordance with claim 11 wherein said isomerization reaction occurs at a pressure in the range of between about 35 psig and about 200 psig.

13. A process for isomerizing 3-methoxy-1,7-octadiene comprising contacting 3-methoxy-1,7-octadiene with an alkanol in the presence of a catalytically effective amount of a catalyst selected from the group consisting of cupric chloride and a mixture of cupric chloride and palladium chloride whereby 8-methoxy-1,6-octadiene is formed.

14. A process in accordance with claim 13 wherein said catalyst is cupric chloride.

15. A process in accordance with claim 13 wherein said catalyst is a mixture of cupric chloride and palladium chloride.

16. A process in accordance with claim 15 wherein said mixture of cupric chloride and palladium chloride is present such that the weight ratio of cupric chloride to palladium chloride is in the range of between about 5:1 and about 100:1.

17. A process in accordance with claim 13 wherein said isomerization process occurs at a temperature in the range of between about 100° C. and about 150° C. and a pressure in the range of between about 50 psig and about 150 psig.

18. A process in accordance with claim 13 wherein said alkanol is selected from the group consisting of methanol, ethanol and isopropanol.

19. A process for isomerizing 3-methoxy-1,7-octadiene comprising contacting 3-methoxy-1,7-octadiene with methanol and a catalytically effective amount of a catalyst selected from the group consisting of cupric chloride and a mixture of cupric chloride and palladium chloride at a temperature in the range of between about 115° C. and 135° C. and a pressure in the range of between about 75 psig and about 125 psig whereby 8-methoxy-1,6-octadiene is formed.

20. A process in accordance with claim 19 wherein said catalyst is cupric chloride.

21. A process in accordance with claim 19 wherein said catalyst is a mixture of cupric chloride and palladium chloride present such that the weight ratio of said cupric chloride to said palladium chloride is in the range of between 15:1 and 25:1.

* * * * *